US006644315B2

(12) United States Patent
Ziaee (10) Patent No.: US 6,644,315 B2
(45) Date of Patent: *Nov. 11, 2003

(54) NASAL MASK (76) Inventor: Saeed Ziaee, 42 Castleridge Dr., Richmond Hill, Ontario (CA), L4B 1P8

( * ) Notice: Subject to any disclaimer, the term of this patent is extended or adjusted under 35 U.S.C. 154(b) by 0 days.

This patent is subject to a terminal disclaimer.

(21) Appl. No.: 10/041,787

(22) Filed: Oct. 19, 2001

(65) Prior Publication Data

US 2002/0053347 A1 May 9, 2002

Related U.S. Application Data (63) Continuation-in-part of application No. 09/593,813, filed on Jun. 15, 2000
(60) Provisional application No. 60/139,721, filed on Jun. 18, 1999.

(51) Int. Cl.[7] .............................................. A62B 18/02
(52) U.S. Cl. .............................. 128/206.21; 128/206.24
(58) Field of Search ................... 128/206.21, 206.11, 128/206.12, 206.13, 206.16–207.18, 203.29, 204.12, 200.24, 201.22, 201.23, 201.26

(56) References Cited

U.S. PATENT DOCUMENTS

| 1,362,766 A | * | 12/1920 | McGargill | 128/206.24 |
| 2,663,297 A | * | 12/1953 | Turnberg | 128/205.25 |
| 4,248,218 A | * | 2/1981 | Fischer | 128/204.18 |
| 4,782,832 A | * | 11/1988 | Trimble et al. | 128/207.18 |
| 4,915,105 A | * | 4/1990 | Lee | 128/205.27 |
| 4,944,310 A | | 7/1990 | Sullivan | 128/848 |
| 4,996,983 A | | 3/1991 | AmRhein | 128/206.11 |
| 5,042,478 A | * | 8/1991 | Kopala | 128/207.18 |
| 5,113,857 A | | 5/1992 | Dickerman et al. | 128/207.18 |
| D333,015 S | | 2/1993 | Farmer et al. | D29/8 |
| 5,243,971 A | * | 9/1993 | Sullivan et al. | 128/205.25 |
| 5,477,852 A | | 12/1995 | Landis et al. | 128/207.18 |
| 5,533,506 A | * | 7/1996 | Wood | 128/207.18 |
| 5,538,000 A | * | 7/1996 | Rudolph | 128/205.25 |
| 5,662,101 A | * | 9/1997 | Ogden et al. | 128/205.25 |
| 5,687,715 A | * | 11/1997 | Landis et al. | 128/207.18 |
| 5,724,965 A | | 3/1998 | Handke et al. | 128/207.13 |
| 5,752,510 A | * | 5/1998 | Goldstein | 128/207.18 |
| 5,832,918 A | * | 11/1998 | Pantino | 128/205.25 |
| D402,755 S | | 12/1998 | Kwok | D24/110.4 |
| 6,019,101 A | * | 2/2000 | Cotner et al. | 128/207.13 |
| D423,096 S | | 4/2000 | Kwok | D24/110.1 |
| 6,044,844 A | * | 4/2000 | Kwok et al. | 128/207.11 |
| 6,112,746 A | | 9/2000 | Kwok et al. | 128/207.13 |
| 6,123,071 A | | 9/2000 | Berthon-Jones et al. | 128/204.18 |
| 6,135,109 A | | 10/2000 | Blasdell et al. | 128/206.28 |
| 6,263,874 B1 | | 7/2001 | LeDez et al. | 128/206.21 |
| 6,431,172 B1 | * | 8/2002 | Bordewick | 128/207.18 |
| 6,467,483 B1 | * | 10/2002 | Kopacko et al. | 128/207.12 |

* cited by examiner

Primary Examiner—Weilun Lo
Assistant Examiner—Teena Mitchell
(74) Attorney, Agent, or Firm—Grossman & Elight, LLC (57) ABSTRACT A nasal mask has a shell portion that is a hollow enclosure with a rearwardly facing opening that is defined by edge portions of the shell portion. A resiliently deformable endless interface member engages and extends around the edge portion of the opening and forms a seal between the shell portion and the user's face. The shell portion and the interface member are generally symmetrical about a median place. The shell portion has two gas inlet orifices, one on each side of the median place. Each orifice is provided with an attachment mechanism upon which is attachable a swivel inlet. The swivel inlets may be rotated through 180 degrees and locked in place.

12 Claims, 9 Drawing Sheets

NASAL MASK

CROSS-REFERENCE TO RELATED APPLICATIONS

This application is a continuation-in-part of co-pending non-provisional application 09/593,813 filed Jun. 15, 2000. Application 09/593,813 claims the benefit of the filing date of provisional application 60/139,721 filed Jun. 18, 1999.

BACKGROUND OF THE INVENTION

The present invention relates to a nasal mask. Known nasal masks of which the applicant is aware have suffered from various disadvantages. For example, known nasal masks do not prevent leakage of gas such as air or oxygen from the mask efficiently, and do not distribute forces evenly on the face of the user. With known masks, an undesirably high tensile force has to be exerted by the straps or other mask retaining devices that hold the mask to the user's head, and as a result excessive pressure tends to be exerted on the user's face, causing breakdown of the skin, for example, on the bridge of the nose. Further, known masks interfere with use of eye glasses while wearing the mask, and may present the difficulty that a gas tube may become pinched or obstructed when the user lies on one side, for example when the user is sleeping.

BRIEF SUMMARY OF THE INVENTION

The present invention provides a shell portion and an interface member for a nasal mask comprising a shell portion defining a hollow enclosure with a rearwardly facing opening defined by edge portions of the shell portion, and a resiliently deformable endless interface member engaging with and extending around said edge portion of the opening and adapted to form a seal between the shell portion and the user's face, and wherein the shell portion and the interface member are at least generally symmetrical about a median plane, and said shell portion has two gas inlet orifices disposed one on each side of the median plane. With this arrangement, the mask may be supplied with gas through two relatively small diameter flexible tubes coupled to the orifices, respectively. The small diameter tubes exert only relatively small tensile forces away from the user's face, and therefore only relatively small forces need to be exerted by retaining straps to retain the mask, and as a result, excessive application of force to the user's face and problems such as breakdown of skin on the bridge of the nose can be avoided. Further, the smaller tubes can be easily oriented in any desired position relative to the mask. For example, they may be positioned downwardly below the mask to facilitate wearing of eye glasses, or may be positioned centrally of the top of the user's head so that they are not obstructed if the user lies on one side.

In a preferred form, the gas inlet orifices are positioned symmetrically with respect to the median plane, and the inner side of the shell adjacent each orifice is provided with an inwardly extending tubular portion for engaging deformable nasal pillows that may form a seal between each orifice and a nostril of the user.

In one aspect, the present invention provides a nasal pillow, for use in combination with a nasal mask, the nasal mask comprising a shell portion and a resiliently deformable endless interface member engaging with and extending around an edge portion of an opening of the shell portion and adapted to form a seal between the shell portion and the user's face, the shell portion having two inlet orifices and tubular pillow engaging members formed integrally with the shell portion and defining a flow passage through the orifices, the nasal pillow including a resiliently deformable corrugated tubular member adapted to be received in the nostrils of a wearer of the mask and to connect with the pillow engaging member, said tubular member comprising a tapering tip, a plurality of relatively narrow intermediate portions and a plurality of relatively wide intermediate portions, and wherein the tip is inclined with respect to the longitudinal axis of the tubular member.

Preferably, the edge portions defining the rearwardly facing opening of the shell are re-entrant edge portions so that the pressures within the mask tend to provide a rearwardly directed component of force tending to resist movement of the mask away from the face of the user. This allows the force applied by the retaining devices to be still further decreased, so that the effects of pressure on the skin of the face of the user may be further alleviated.

In another aspect, the present invention provides a shell portion for a nasal mask, the shell portion defining a hollow enclosure with a rearwardly facing opening defined by edge portions of the shell portion, and wherein the shell portion is at least generally symmetrical about a median plane, and the shell portion having two gas inlet orifices disposed one on each side of the median plane, the shell portion further including an attachment mechanism formed integrally with each orifice of the shell portion; and a swivel inlet adapted to be connected to each attachment mechanism and defining a flow passage through the orifice, the swivel inlet comprising a hollow cylindrical inlet tube having an elbow portion, and wherein the swivel inlet is rotatable around the axis of the attachment mechanism.

Preferred embodiments of the present invention will now be described in more detail, by way of example only, with reference to the accompanying drawings.

BRIEF DESCRIPTION OF THE SEVERAL VIEWS OF THE DRAWINGS

Reference will now be made, by way of example, to the accompanying drawings which show a preferred embodiment of the present invention, and in which:

FIG. 17b shows a cross-section of the swivel inlet taken along the line 17—17 in FIG. 17a.

DETAILED DESCRIPTION OF THE INVENTION

Referring to the drawings wherein like reference numerals indicate like parts, a mask 20 comprises a shell portion 21 and an interface portion 22, preferably used in combination with pillow engaging members 23 and nasal pillows 24.

Figure 4:
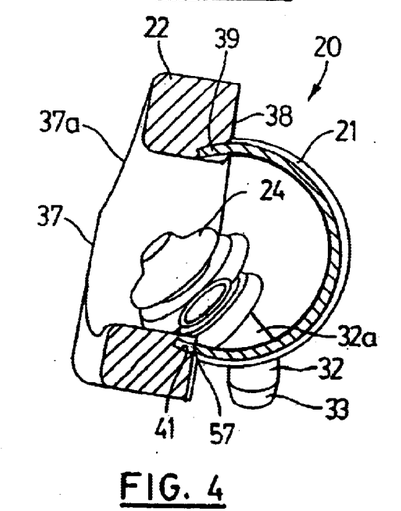
FIG. 4 shows a cross-sectional view taken on the line 4—4 in FIG., 3.

As best seen in FIGS. 1, 2, 4 and 5 shell portion 21 defines a hollow enclosure with a rearwardly facing generally triangular opening 26 defined by edges of the shell comprising a transverse top portion 27, arcuately transversely outwardly and downwardly extending side portions 28 and arcuate lower edge portions 29. The shell 21 is generally symmetrical about a median plane 3 seen in FIG. 2, and the shell portion 21 has two gas inlet orifices comprising openings 31 in the lower front portion of the shell 21. Adjacent each opening 31, the shell 21 is formed integrally with outwardly extending tubular portions 32 having slightly tapering end portions 33 defining a flow passage extending from the outer end of the tubular portions to the interior of the shell 21 through the openings 31. In the preferred form, inwardly of the shell 21 and integrally formed therewith are inwardly extending tubular portions 32a that, as seen in FIG. 4, each have their axes inclined somewhat downwardly rearwardly with respect to the axis of the outer portion 32.

In the preferred form, shell 21 comprises two part spherical portions 34 that are connected together along a bridging portion 36 coincident with the median plane. The spherical portions 34 provide especially good symmetry and distribute pressure evenly on the wearer's face and provide reentrant portions providing rearwardly directed forces urging the mask toward the wearer's face.

Each portion 34 has on each transversely outer side, at a portion intermediate the front and rear sides of the shell 21, an integrally formed strap lug 35 to which a retaining strap may be attached.

The shell portion 21 may, for example, be molded of a stiffly resilient plastics material.

The interface member 22 is preferably formed of a soft, compliant and resiliently deformable material, for example a soft silicone rubber composition that provide a cushion between the rigid shell 21 and the patient's face and conforms to and seals to the patient's face on the one hand and to the shell 21 on the other.

Figure 1:
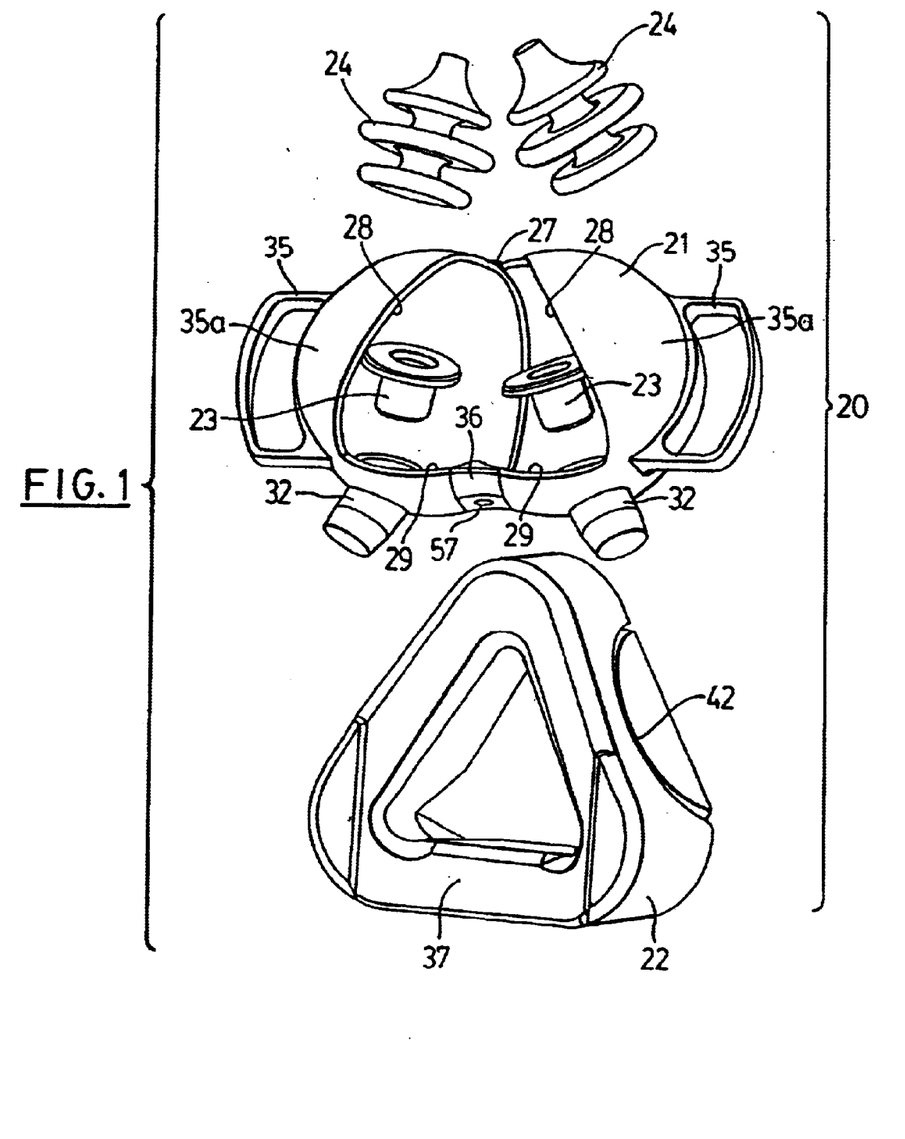
FIG. 1 shows an exploded view form the rear of a nasal mask in accordance with the invention.
Figure 6:
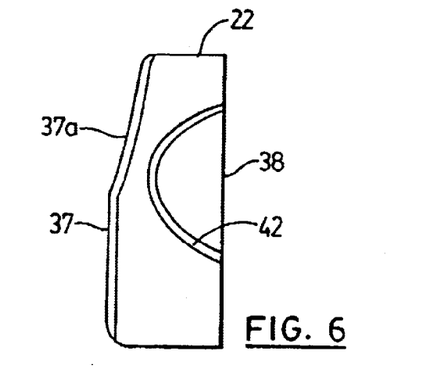
FIG. 6 is a side view of the interface portion of the mask.
Figure 7:
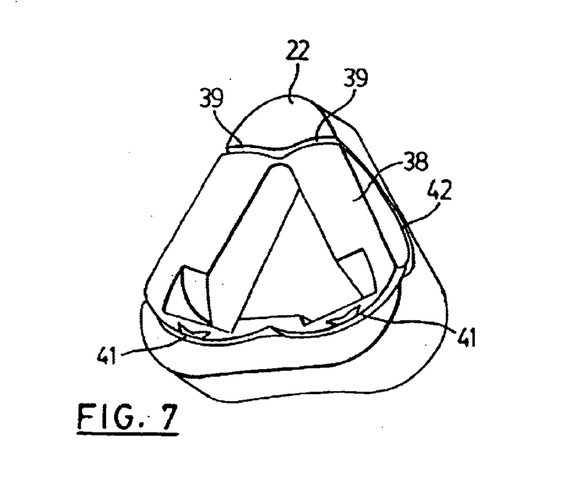
FIG. 7 is an isometric view from the front of the interface portion.

As best seen in FIGS. 1, 6 and 7, the interface 22 comprises a generally triangular endless member with rounded corners and generally planar rear and front sides 37 and 38 that, in use, engage with the patient's face and with the shell 21, respectively. As seen in FIG. 4, the rear side 37 of the interface member 22 may incline slightly forwardly upwardly at 37a, so that the member 22 tapers slightly in thickness upwardly and tends to conform to the patient's cheeks on each side of the nose.

Figure 2:
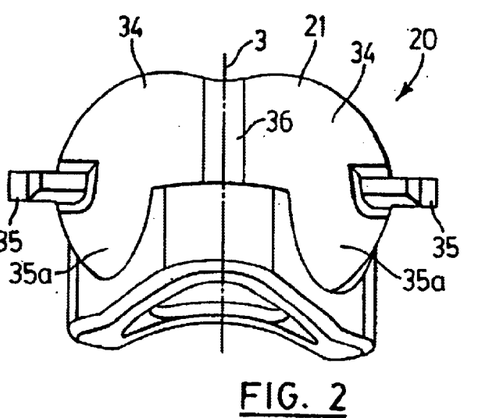
FIG. 2 is a top plan view of the mask of FIG. 1 in assembled condition.
Figure 3:
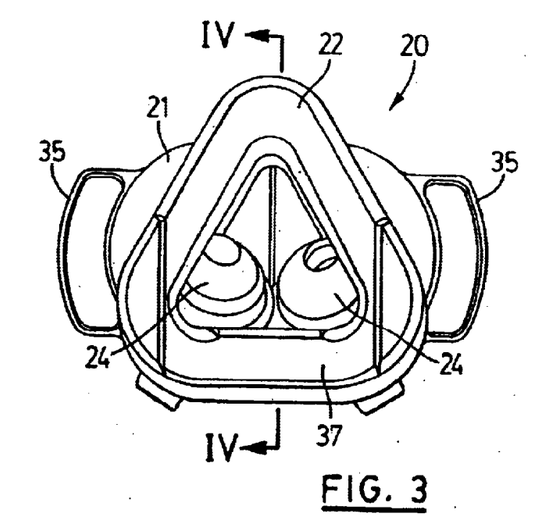
FIG. 3 is a view from the rear of the mask in the assembled condition.

The upper portion of the front face 38 of the interface member 22, as best seen in FIG. 7 is formed with a series of part circular grooves that receive the edges of the shell portion 21 when the interface is applied to the shell portion in the assembled condition as seen in FIGS. 2 to 4. As best seen in FIG. 7, these grooves are symmetrical about the median plane and comprise upper part circular grooves 39 that receive the bridge portion 36 and upper portions of the edges 28, and lower part circular grooves 41 that receive the lower edges 29 and lower portions of the side edges 28. Further, the sides of the interface portion 22 are formed with part circular grooves 42 that receive the intermediate portions of the side edges 28.

Figure 4A:
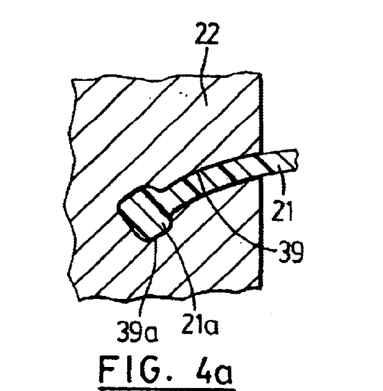
FIG. 4a is a partial cross-sectional view on an enlarged scale showing a modification of the structure of FIG. 4.
Figure 5:
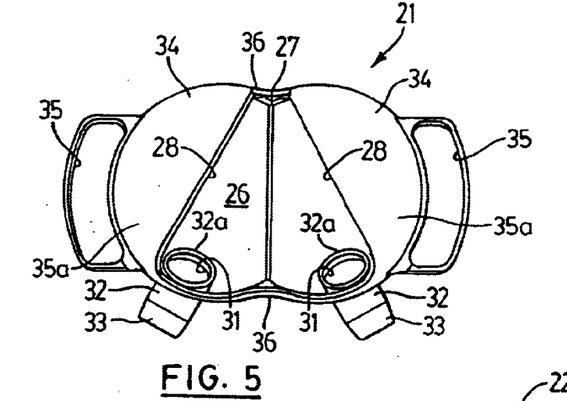
FIG. 5 is a view from the rear of the shell portion of the mask.

As best seen in FIG. 4, the grooves preferably penetrate a depth of at least about 25% of the thickness of the interface 22. Preferably, the grooves are slightly narrower than the thickness of the shell 21, so that there is a resilient reaction tending to cause the sides of the grooves to grip tightly on the edges of the shell 21. As shown in FIG. 4a, the edges of the shell 21 may be formed with a thickened bead 21a, and the bottom of each of the grooves such as groove 39 in the interface 22 may be formed with an enlarged recess 39a of somewhat smaller dimensions than the bead 21a, so that there is a resilient reaction tending to cause the material of the interface 22 to grip resiliently on the enlarged bead 21a, and improve the security of attachment of the interface 22 to the shell 21.

It will be noted that the interface member 22 is removably connected to the shell portion 21 so that it can be detached and a somewhat smaller or larger interface member substituted, in order to improve the fit of the interface member to the face of the patient.

Optionally, the mask may be used with nasal pillows 24 that are mounted on pillow engaging members 23. However, the use of such nasal pillows is not essential, and it is contemplated the mask may be used without such nasal pillows.

Figure 10:
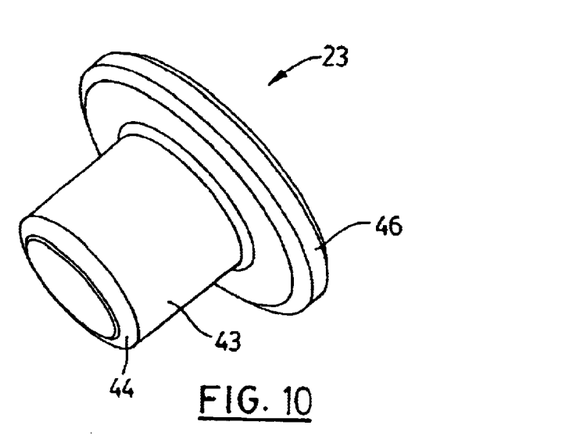
FIG. 10 is an isometric view from the rear and below of a disk member optionally forming part of the mask.
Figure 11:
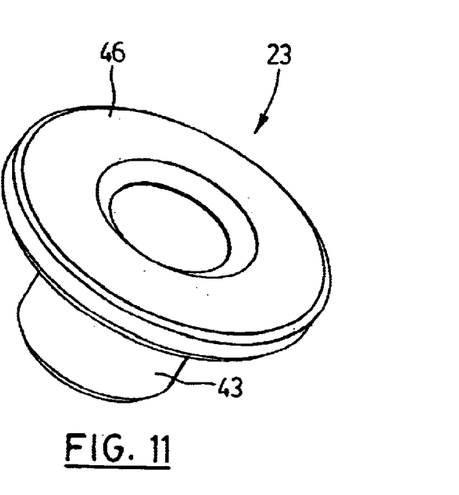
FIG. 11 shows an isometric view from above and from one side of the disk member.

As seen in FIGS. 10 and 11, the pillow engaging members 23, which may be molded of rigid plastics material, comprise hollow cylindrical stem portions 43 with tapering lower ends 44, and formed integrally with an enlarged disk element 46.

Figure 8:
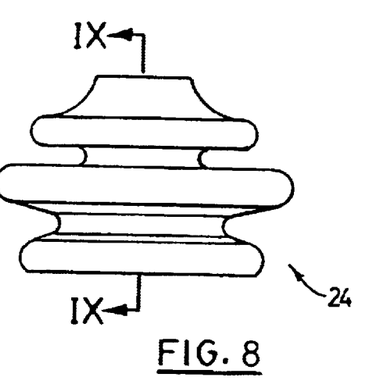
FIG. 8 is a side view of a nasal pillow optionally forming a portion of the mask.
Figure 9:
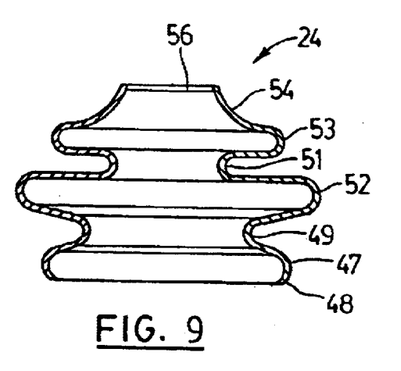
FIG. 9 is a cross-section along the line 9—9 in FIG. 8.

The nasal pillows 24, as best seen in FIGS. 8 and 9 are preferably formed of a highly resiliently deformable soft plastics material, for example soft silicone rubber composition.

The pillow is of a generally corrugated or accordion-pleated structure have a wide base portion 47 with re-entrant lower edges 48, relatively narrow intermediate portions 49 and 51, and relatively wide portions 52 and 53, the upper most of these terminating in an upwardly arcuately tapering tip 54 having a circular opening 56 at the upper edge.

In use, a disk element 46 of a member 23 is inserted within one of the wider portions 48, 52 or 53 of the nasal pillow 24 by stretching the material of the pillow 24, so that the disk element 46 snap-fits within one of the wider portion. The nasal pillows together with the members 23 are then inserted within the mask, and the stem portions 43 inserted within the inwardly extending cylindrical tubular portions 32a of the shell 21, as seen in FIGS. 3 and 4. The position of the pillows 24 within the mask may be adjusted to enable the tapering tip portions 54 of the pillows to engage snugly and in a leak free manner within the nostrils of a patient. This adjustment is effected by engaging the disk element 46 with a higher or with a lower one of the wider portions 47, 52 or 53.

Figure 15:
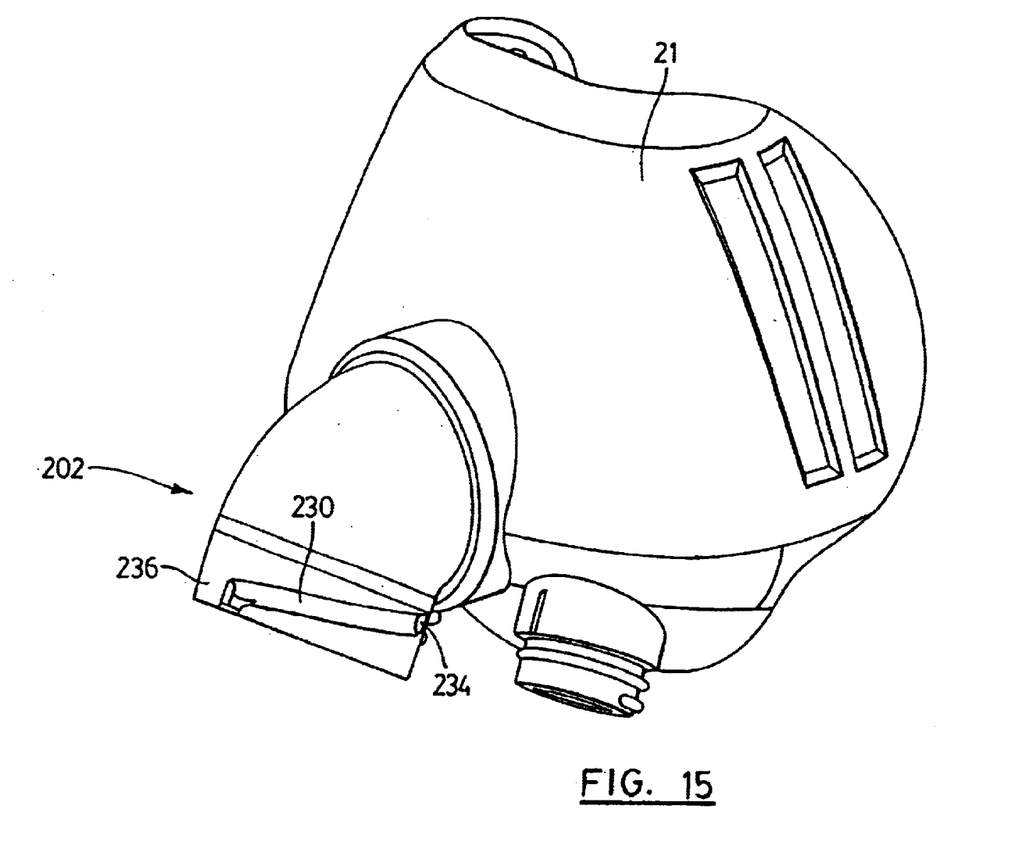
FIG. 15 shows a cross-section taken along the center-line of the mask 15—15 shown in FIG. 13.

In another embodiment, an extended pillow 70, as shown in FIG. 15, is attached to the inwardly extending cylindrical tubular portions 32a of the shell 21. Like the pillow 24, the extended pillow 70 is of a generally corrugated or accordion-pleated structure having a wide base portion with re-entrant lower edges, relatively narrow intermediate portions, and relatively wide portions, the upper most of these terminating in an upwardly arcuately tapering tip 54 having a circular opening 56 at the upper edge. However, the tip 54 of the extended pillow 70 is angled with respect to the longitudinal axis of the extended pillow 70. As shown in FIG. 15, the extended pillow 70 is mounted upon the inwardly extending cylindrical tubular portion 32a in such a manner that the intermediate and wide portions of the extended pillow 70 extend substantially horizontally towards the patient's face, whereas the tip 54 angles upwards towards the patient's nostril. The extended pillow 70 flexes easily to accommodate downwards forces at the tip 54. Advantageously, this provides a gentle and flexible contact point for the patient's nostrils, thereby avoiding irritation or abrasion.

Desirably, the shell 21 is provided with a small vent hole 57 in a lower portion of the bridge portion 36 of the shell, so that excessive pressure does not build up within the shell 21, for example when the mask 20 is applied and tightened to the user's face. If desired, this hole 57 may be plugged with a tight-fitting resilient e.g. rubber plug.

Figure 12:
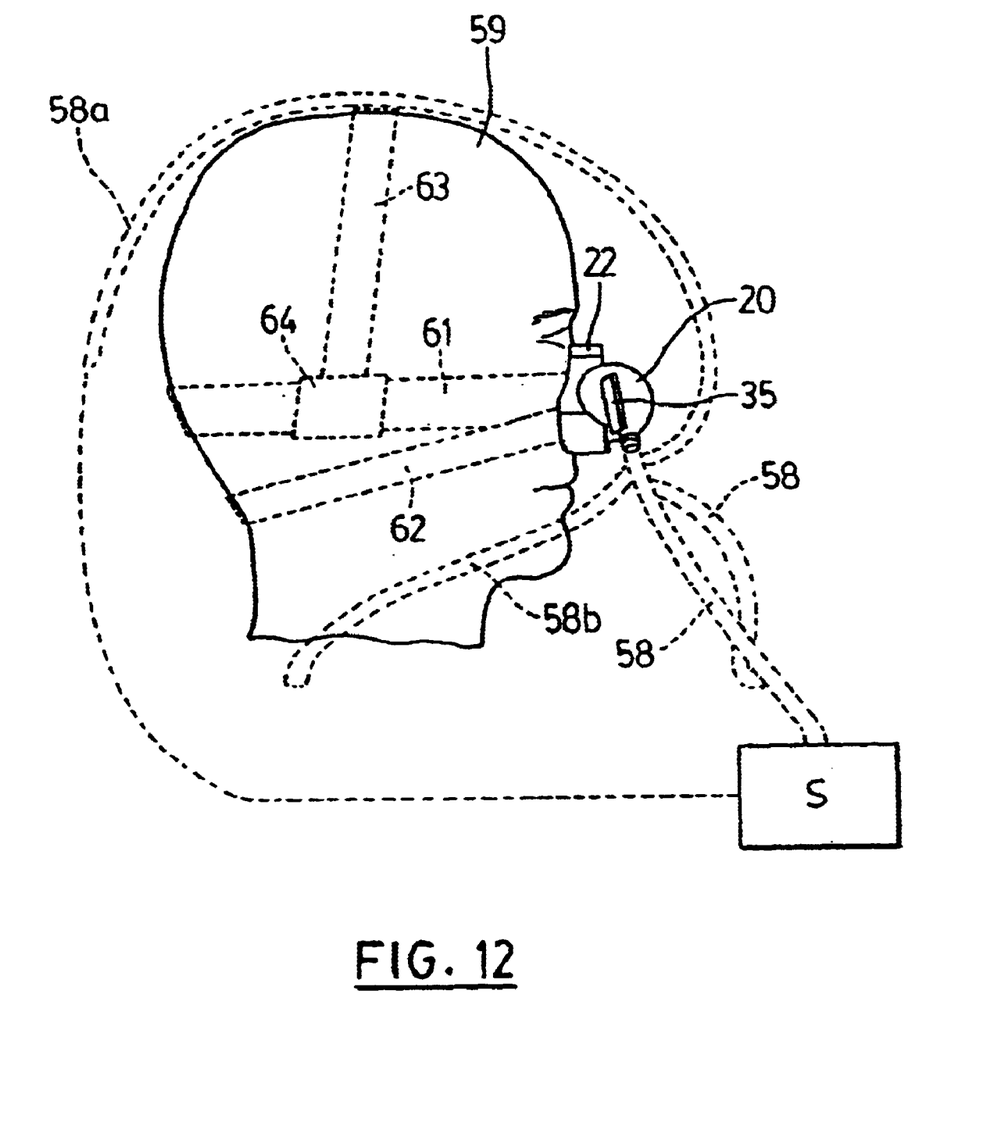
FIG. 12 shows somewhat schematically the mask worn by a patient.

In use, as seen in FIG. 12, a relatively small diameter gas or air supply hose 58 is push fitted over each outer cylindrical tubular portion 32, as shown in broken lines in FIG. 12, and is connected to a source S of air or other gas to be supplied to the patient. A strap or straps are attached through the strap lugs 35, and are passed around the head 59 to retain the mask 20 with the interface 22 pressed firmly and in a leak free fashion against the bridge of the nose, upper lip and cheeks on either side of the nose as seen in FIG. 12. Preferably, as seen in FIG. 12, the straps comprise a first strap 61 passing around the back of the patient's head 59, a second strap 62 passing around the head 59 at a region lower than strap, and a third strap 63 connected to intermediate portions 64 of strap 61 on each side of the patient's head 59 and passing over the top of the head 59. The straps 61 to 63 are usually resilient and may incorporate buckles or the like whereby the tension in each strap may be adjusted.

The relatively small diameter tube 58 exert only relatively small tensile forces in the direction away from the face of the patient and therefore only relatively small forces need to be exerted by the straps 61 and 62 to retain the mask 20 and, as a result, excessive application of force to the user's face can be avoided. Pressure differentials over ambient existing in the inside of the shell 21 tend to bias the mask 20 toward the user's face as a result of the reaction of the pressure against the re-entrant portions 35a of the shell that extend rearwardly transversely inwardly between the lugs 35 and the edges 28 of the opening 26, so that excessive force exerted by the strap 59 can be avoided without risking leaks from the mask. The small diameter tubes may be easily oriented in any desired position relative to the mask 20. For example, they may be positioned downwardly below the mask as indicated for the tubes 58 in FIG. 12, they may be positioned centrally of the top of the user's head, as indicated by reference numeral 58a in FIG. 12, so that they are not obstructed if the user lies on one side, for example, when sleeping, or they may pass rearwardly on one side or on each side of the patient's head 59, as indicated by reference numeral 58b in FIG. 12, to a source placed behind the user.

When the nasal pillows 24 are employed, an especially leak free delivery of gas to the patient's airways can be provided, so that gas supplied at a selected pressure from the source S can be delivered to the patient without leaks and pressure loss occurring.

Figure 13:
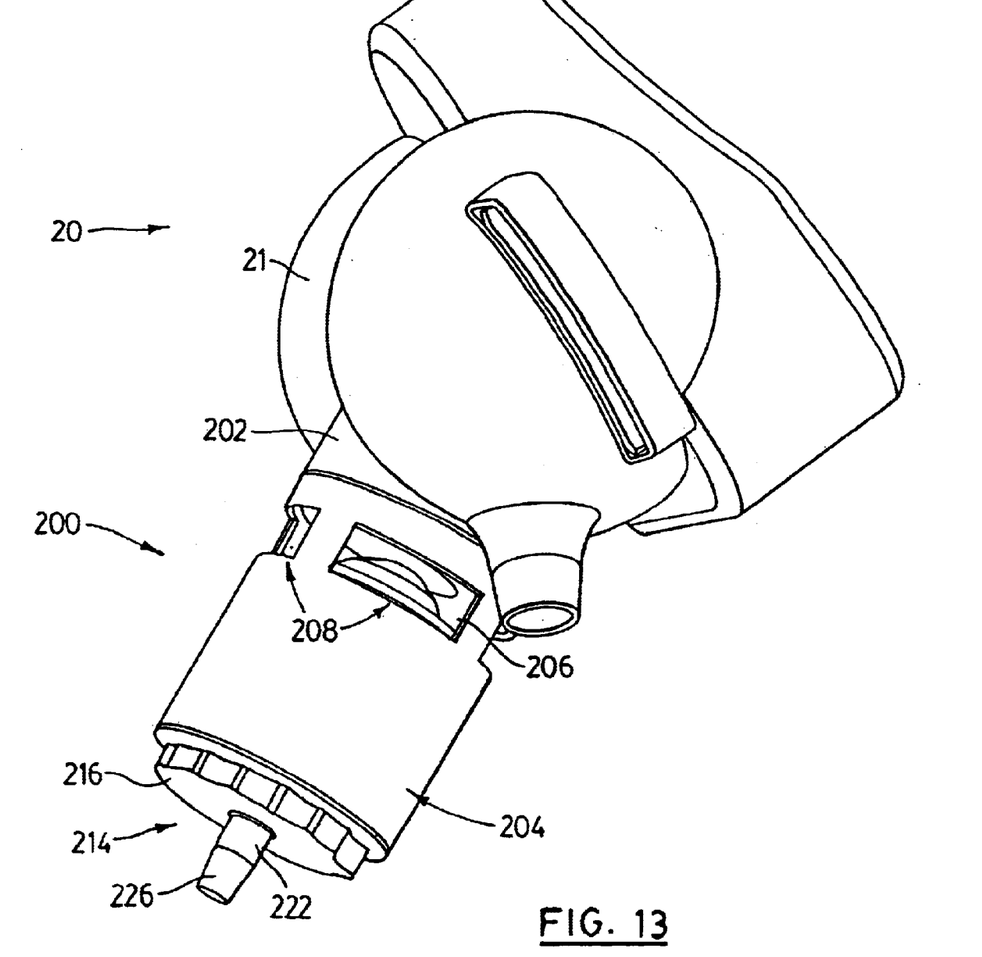
FIG. 13 shows an isometric view from the rear and above of the mask including extended pillows and swivel inlets.
Figure 14:
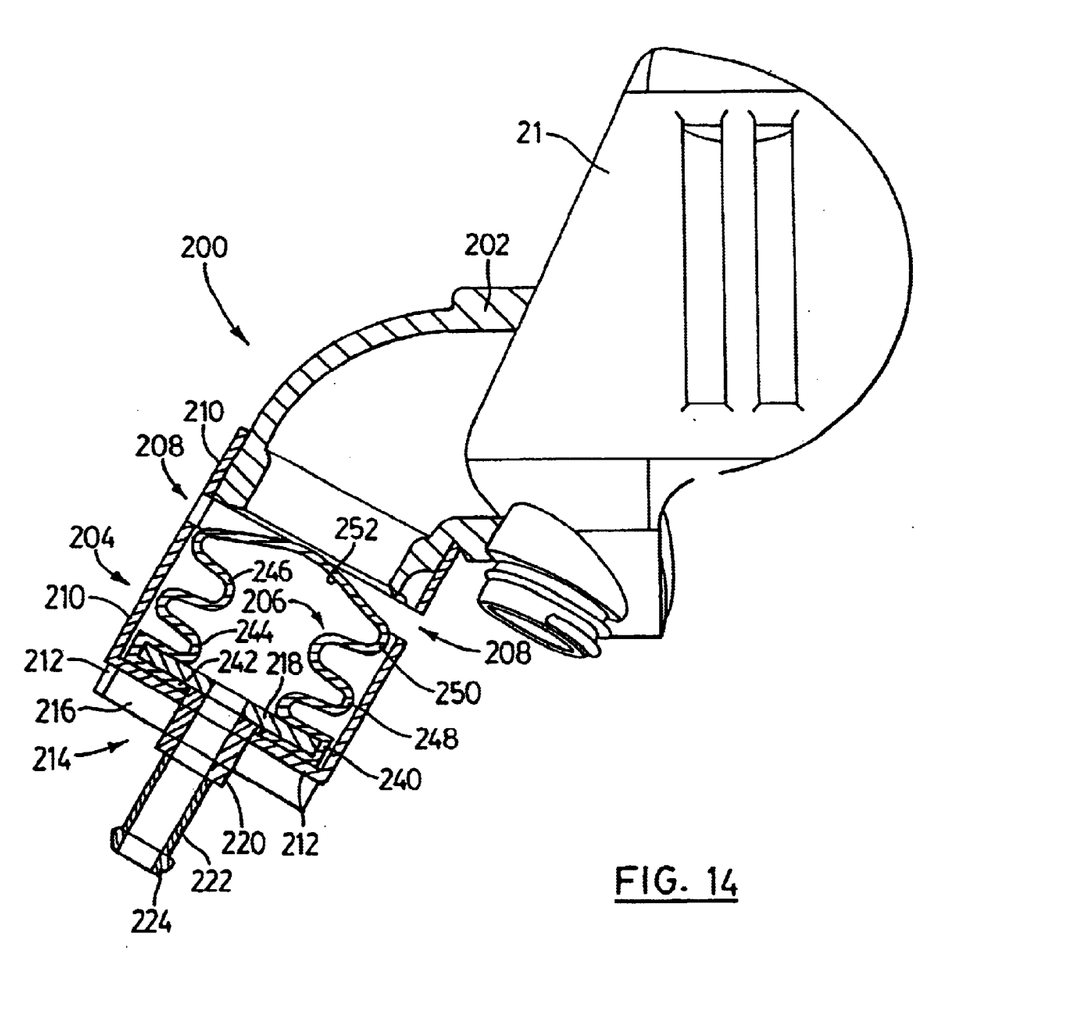
FIG. 14 shows an exploded isometric view of the mask including extended pillows and swivel inlets.

Reference is now made to FIGS. 13 through 15 which show the mask 20 including swivel inlets 72. Each swivel inlet 72 may be molded of a stiffly resilient plastics material and comprises a hollow cylindrical stem portion 74, a hollow elbow portion 76 and a hollow attachment portion 78. The stem portion 74 is in communication with the elbow portion 76, which is in communication with the attachment portion 78, thereby resulting in a cylindrical passage through the swivel inlet 72.

The outwardly extending tubular portions 32 of the shell 21 further include an attachment mechanism 80 for attaching the swivel inlets 72 to the shell 21. In use, a gas or air supply hose is push fitted over the stem portion 74 of the swivel inlets 72, so as to provide air or other gas to the patient.

Figure 17A:
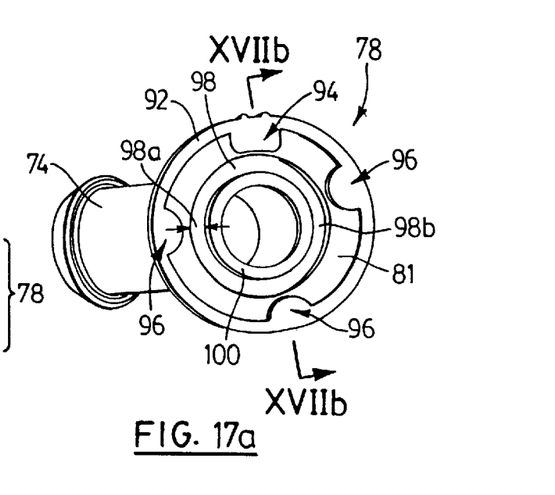
FIG. 17a shows an perspective view from above of a swivel inlet.
Figure 17B:
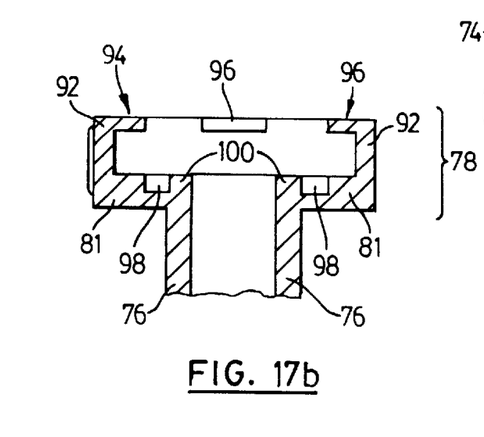

Reference is now made to FIG. 17a which shows an isometric view from above of a swivel inlet and FIG. 17b which shows a cross-section of the swivel inlet taken along the line 17—17 in FIG. 17a. The attachment portion 78 of the swivel inlet 72 includes a flat circular flange 81. Extending upwards around the perimeter of the flange 81 is a rim 92. Projecting inwards from the upper surface of the rim 92 and displaced above the flange 81 are multiple rounded tabs 96 and a square tab 94. The flange 81 has within its upper surface a circular channel 98, which defines an inner tube 100. The circular channel 98 has a non-uniform width, tapering from a wide side 98a to a narrow side 98b.

Figure 16:
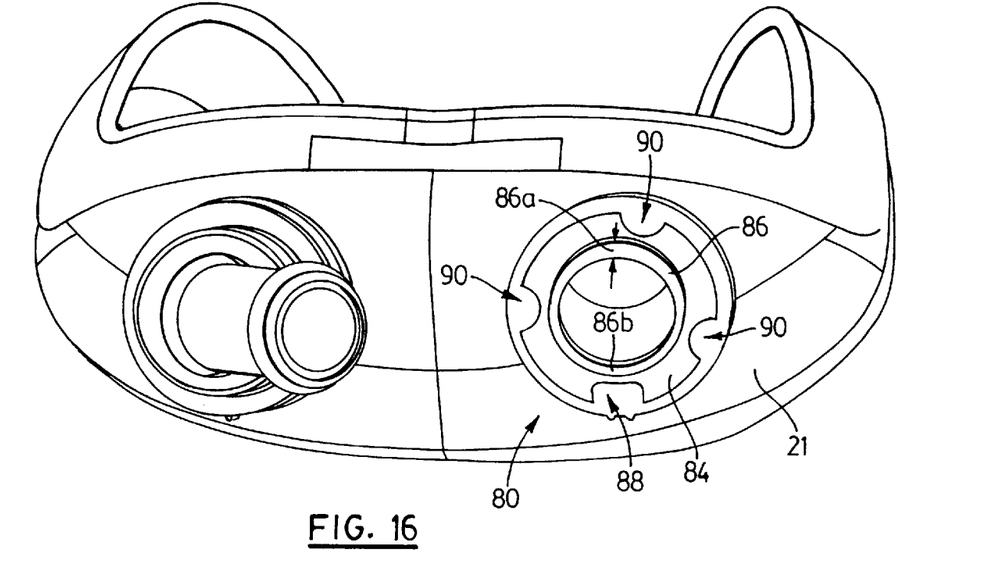
FIG. 16 shows a perspective view from the bottom of the shell portion of the mask, including one attached swivel inlet.

Referring now to FIG. 16, which shows an isometric view of the shell 21 including the attachment mechanism 80, the attachment mechanism 80 includes an attachment tube 86 and a key 84, as shown in FIG. 14. The key 84 is displaced around and extends outwardly from the attachment tube 86. The key 84 is spaced away from the front surface of the shell 21. Referring again to FIG. 16, it may be seen that the attachment tube 86 has a non-uniform thickness, tapering from a wide portion 86a to a narrow portion 86b.

Multiple rounded notches 90 and one square notch 88 are located about the circumference of the key 84. The shape of the key 84 created by the notches 88 and 90 corresponds to the shape of the attachment portion 78 created by the inner perimeter of the rim 92 and the tabs 94 and 96. Accordingly, the swivel inlets 72 may be attached to the attachment mechanism 80 by aligning the tabs 94 and 96 and the notches 88 and 90. Thereupon, the rim 92 of the swivel inlet 72 will fit over the key 84 and the attachment tube 86 will engage the circular channel 98 in the flange 81. The attachment tube 86 communicates with the inner tube 100 of the swivel inlet 72, so as to create a continuous passage therethrough. By providing an irregular key 84 shape, attachment of the swivel inlet 72 to the attachment mechanism 80 may occur only at a particular rotational alignment.

Once the swivel inlet 72 is fitted onto the attachment mechanism 80, it may be rotated about the central axis of the attachment mechanism 80, thereby swivelling the stem portion 74. Due to the non-uniform thickness of the attachment tube 86 and the circular channel 98, the swivel inlet 72 may only be rotated through 180 degrees. The swivel inlet 72 rotates relatively smoothly through 150 degrees, then with some increased frictional resistance to 180 degrees as the increasing thickness of the attachment tube 86 resiliently deflects the sides of the circular channel 98 outwardly, at which point further rotational movement of the swivel inlet 72 is prevented by the increasing thickness of the attachment tube 86 in cooperation with the decreasing width of the circular channel 98. Similarly, when fitted onto the attachment mechanism 80, the swivel inlet 72 may only rotate in one direction, rotation in the other direction being prevented by the thick portion 86a of the attachment tube 86 in cooperation with the narrow side 98b of the circular channel 98. When rotated through 150 degrees, the engagement of the thick portion 86a of the attachment tube 86 with the narrow side 98b of the circular channel locks the swivel inlet into a rotational position wherein further rotational movement is frictionally resisted.

In one embodiment, the key 84 shape and swivel inlet 72 are arranged such that the swivel inlet 72 may only be attached to the attachment mechanism 80 at a rotational alignment wherein the stem portion 74 is angled inwards towards the centre of the shell 21. The swivel inlet 72 may then be rotated in one direction past 150 degrees and up to 180 degrees, wherein the stem portion 74 becomes frictionally locked in an alignment angled away from the centre of the shell 21, and thus away from the user's mouth. This arrangement enables the user to lock the swivel inlets 72 in a position angled away from the mouth to allow eating or drinking.

The present invention may be embodied in other specific forms without departing from the spirit or essential characteristics thereof. Certain adaptations and modifications of the invention will be obvious to those skilled in the art. Therefore, the above discussed embodiments are considered to be illustrative and not restrictive, the scope of the invention being indicated by the appended claims rather than the foregoing description, and all changes which come within the meaning and range of equivalency of the claims are therefore intended to be embraced therein.

I claim:

1. A shell portion for a nasal mask, said shell portion defining a hollow enclosure with a rearwardly facing opening defined by edge portions of the shell portion, and wherein the shell portion is at least generally symmetrical about a median plane, and said shell portion having at least one gas inlet orifice disposed one on each side of the median plane, said shell portion further comprising:
   an attachment mechanism formed integrally with the at least one orifice of the shell portion; and
   a swivel inlet adapted to be connected to the attachment mechanism and defining a flow passage through said at least one orifice, said swivel inlet comprising a hollow cylindrical inlet tube having an elbow portion, and wherein said swivel inlet is rotatable around an axis of said attachment mechanism.

2. A shell portion for a nasal mask, as defined in claim 1, wherein said attachment mechanism comprises (1) an outwardly extending tubular portion defining a flow passage through said orifice and (2) a generally circular key shape, and wherein said swivel inlet further comprises an outer tube attached to and coaxial with said inlet tube, wherein an end of said outer tube has tabs extending inwards therefrom towards said inlet tube, an inner perimeter of said outer tube and said tabs defining a key slot corresponding to said key shape.

3. A shell portion for a nasal mask, as defined in claim 2, wherein said inlet tube and said tubular portion are adapted to be coaxially fitted together to permit axial rotation with respect to each other.

4. A shell portion for a nasal mask, as defined in claim 1, wherein said swivel inlet further comprises a generally circular key shape, and wherein said attachment mechanism comprises an outwardly extending tubular portion defining a flow passage through said at least one orifice and an outer tube attached to and coaxial with said tubular portion, wherein an end of said outer tube has tabs extending inwards therefrom towards said tubular portion, an inner perimeter of said outer tube and said tabs defining a key slot corresponding to said key shape.

5. A shell portion for a nasal mask, as defined in claim 4, wherein said inlet tube and said tubular portion are adapted to be coaxially fitted together to permit axial rotation with respect to each other.

6. A shell portion for a nasal mask, as defined in claim 1, wherein said attachment mechanism comprises an outwardly extending tubular portion defining a flow passage through said at least one orifice, and wherein said swivel inlet further comprises a flange extending outwardly from said inlet tube, said flange having formed therein a channel adapted to receive said tubular portion in mating engagement therewith.

7. A shell portion for a nasal mask, as defined in claim 6 wherein said tubular portion has a first side of a first thickness and a second side of a second thickness, said first thickness being thicker than said second thickness, and said tubular portion tapering in thickness from said first side to said second side.

8. A shell portion for a nasal mask, as defined in claim 7 wherein said channel has a first side of a first width and a second side of a second width, said first width being wider than said second width, and said channel tapering in width from said first side to said second side.

9. A shell portion for a nasal mask, as defined in claim 8, wherein said channel and said tubular portion are adapted to permit limited rotation around an axis of said tubular portion and to frictionally resist further rotation of said swivel inlet around the axis of said tubular portion.

10. A shell portion for a nasal mask, as defined in claim 9, wherein said limited rotation comprises about 180 degrees.

11. A shell portion for a nasal mask, as defined in claim 1, wherein said attachment mechanism and said swivel inlet are adapted to permit limited rotation of said swivel inlet around the axis of said attachment mechanism and to frictionally resist further rotation of said swivel inlet around the axis of said tubular portion.

12. A shell portion for a nasal mask, as defined in claim 11, wherein said limited rotation comprises about 180 degrees.

* * * * *